US010150998B2

(12) United States Patent
Martin

(10) Patent No.: US 10,150,998 B2
(45) Date of Patent: Dec. 11, 2018

(54) GENETIC TEST

(71) Applicant: Mars, Incorporated, McLean, VA (US)

(72) Inventor: Alan Martin, Waltham-on-the-Wolds (GB)

(73) Assignee: MARS, INCORPORATED, McLean, VA (US)

(*) Notice: Subject to any disclaimer, the term of this patent is extended or adjusted under 35 U.S.C. 154(b) by 92 days.

(21) Appl. No.: 14/897,670

(22) PCT Filed: Jun. 10, 2014

(86) PCT No.: PCT/EP2014/061966
§ 371 (c)(1),
(2) Date: Dec. 11, 2015

(87) PCT Pub. No.: WO2014/198686
PCT Pub. Date: Dec. 18, 2014

(65) Prior Publication Data
US 2016/0122822 A1 May 5, 2016

(30) Foreign Application Priority Data

Jun. 13, 2013 (GB) .................................. 1310558.0

(51) Int. Cl.
C07H 21/04 (2006.01)
C12Q 1/68 (2018.01)
C12Q 1/6883 (2018.01)
G06F 19/22 (2011.01)

(52) U.S. Cl.
CPC ........... *C12Q 1/6883* (2013.01); *G06F 19/22* (2013.01); *C12Q 2600/124* (2013.01); *C12Q 2600/156* (2013.01)

(58) Field of Classification Search
None
See application file for complete search history.

(56) References Cited

U.S. PATENT DOCUMENTS 6,261,591 B1  7/2001 Kealy
2013/0263294 A1 10/2013 Martinez et al.

FOREIGN PATENT DOCUMENTS

EP  2123775  11/2009

OTHER PUBLICATIONS

Guo et al. (Osteoarthritis and Cartilage, vol. 19, pp. 420-429, 2011). (Year: 2011).*
Lavrijsen et al. (PLOS One, vol. 9, Issue 1, e87735, Jan. 2014) (Year: 2014).*
Safra et al. (Veterinary Journal, vol. 189, pp. 220-226, 2011) (Year: 2011).*
Tiira et al. (PLoS ONE, vol. 7, No. 7, e41684, Jul. 2012) (Year: 2012).*
Tacher et al. (J. of Heredity, vol. 96, No. 7, pp. 812-816, 2005) (Year: 2005).*
Altschul, "A Protein Alignment Scoring System Sensitive at All Evolutionary Distances", J. Mo. Evol., 1993, 36, pp. 290-300.
Altschul, et al., "Basic Local Alignment Search Tool", J. Mol. Biol., 1990, 215, 403-410.
Barrett, et al., "Haploview: Analysis and Visualization of LD and Haplotype Maps", Bioinformatics vol. 21 No. 2 2005, pp. 263-265, Aug. 5, 2004, 263-265.
Bouwman, et al., "A Bayesian approach to detect QTL affecting a simulated binary and quantitative trait", BMC Proceedings, 2011, 5(Suppl 3): S4-S6.
Cotton, et al., "Reactivity of cytosine and thymine in single-base-pair mismatches with hydroxylamine and osmium tetroxide and its application to the study of mutations", Proc. Natl. Acad. Sci. USA vol. 85, pp. 4397-4401, Jun. 1998, 4397-4401.
Devereux, et al., "A Comprehensive Set of Sequence Analysis Programs for the VAX", Nucleic Acids Research, 1984, 12, pp. 387-395.
Doe, et al., "Transgenic Overexpression of the α7 Integrin Reduces Muscle Pathology and Improves Viability in the dyW Mouse Model of Merosin-Deficient Congenital Muscular Dystrophy Type 1A", Journal of Cell Science, 124, 2287-2297, 2011.
Ganey, et al., "Basement Membrane Composition of Cartilage Canals During", The Anatomical Record, 241:425-437 (1995).
Hagiwara, "Branched-Chain Amino Acids Prevent Insulin-Induced Hepatic Tumor Cell Proliferation by Inducing Apoptosis Through mTORC-1 and mTORC2-Dependent Mechanisms", Journal of Cellulor Physiology, (2012), 227:2097-2105.
Harts, et al., "Mutation Detection by Fluorescent Chemica Cleavage: Application to Hemophilia B", Cold Spring Harbor Laboratory Press, ISSN 1054-9803/94 vol. 3:268-271, 1994, 268-271.
Henikoff, et al., "Amino Acid Substitution Matrices from Protein Blocks", Proc. Natl. Acad. Sci. USA vol. 89, pp. 10915-10919.
Iezzi, "Deacetylase Inhibitors Increase Muscle Cell Size by Promoting Myoblast Recruitment and Fusion through Induction of Follistatin", Developmental Cell, vol. 6, 673-684, May 2004.
Illumina, "CanineSNP20 BeadChip. Retrieved from http://www.illumina.com/Documents/products/datasheets/datasheet_canine_snp20.pdf", Illumina SNP Genotyping, 2007.
Ineke, et al., "Genome Wide Analysis Indicates Genes for Basement Membrane and Cartilage Matrix Proteins as Candidates for Hip Dysplasia in Labrador Retrievers", , PLOS ONE, vol. 9, No. 1, e87735, Jan. 30, 2014.
Izu, et al., "Distribution of Type VI Collagen in the Cartilaginous Tissue of the Proximal Tibia in the Domestic Cat", J. Vet. Med. Sci., 67(9): 927-933, 2005.
Karlin, et al., "Applications and Statistics for Multiple High-Scoring Segments in Molecular Sequences", Proc. Natl. Acad. Sci. USA vol. 90 pp. 5873-5877, Jun. 1993, 5873-5877.
Kealy, "Effects of Dietary Electrolyte Balance on Subluxation of the Femoral Head in Growing Dogs", Am. J. Vet. Res., 1993; 54:555-562.

(Continued)

*Primary Examiner* — Jeanine A Goldberg
(74) *Attorney, Agent, or Firm* — Baker Botts L.L.P.

(57) ABSTRACT

The present invention relates to a method of determining the susceptibility of a dog to, or the likelihood that a dog is protected from, hip dysplasia. The present invention uses mutations linked to canine hip dysplasia to generate a model predicting disease.

5 Claims, No Drawings

(56) References Cited

OTHER PUBLICATIONS

Kohler, et al., "Continuous Cultures of Fused Cells Secreting Antibody of Predefined Specificity", Journal of Immunology, Nature vol. 256 (5517): 495-497, Aug. 1975, 495-497.

Kozhemyakina, et al., "Parathyroid Hormone-Related Peptide Represses Chondrocyte Hypertrophy through a Protein Phosphatase 2A/Histone Deacetylase 4/MEF2 Pathway", Molecular and Cellular Biology, Nov. 2009, vol. 29, No. 21, pp. 5751-5762.

Krontveit, et al., "Risk Factors for Hip-Related Clinical Signs ina Prospective Cohort Study of Four Large Dog Breeds in Norway", Preventive Veterinary Medicine, 103 (2012) 219-227.

Lavrijsen, et al., "Genome wide association analysis of Canine Hip Dysplasia in Labrador Retrievers", Department of Clinical Sciences of Companion Animals, Division of Diagnostic Imaging, Faculty of Veterinary Medicine, Utrecht University, P.O. Box 80154, 3508TD Utrecht, The Netherlands c . . . Centre for Pet Nutrition.

Lifeextension, "Muscular Dystrophy", Downloaded from http://www.lifeextension.com/protocols/neurological/muscular-dystrophy_01.htm.

Lopate, "Congenital Muscular Dystrophy Workup", Available online at http://emedicine.medscape.com/article/1180214-workup.

Maddox, et al., "Elevated Serum Levels in Human Pregnancy of a Molecule Immunochemically Similar to Eosinophil Granule Major Basic Protein", J. Exp. Med. The Rockefeller University Press vol. 158, pp. 1211-1226, Oct. 1983, 1211-1226.

Muntoni, et al., "The Congenital Muscular Dystrophies in 2004: A Century of Exciting Progress", Neuromuscular Disorders, 14 (2004) 635-649.

NCBI, "SH3BP4 SH3 Domain Binding Protein. Retrieved Aug. 16, 2011, from http://www.ncbi.nlm.nih.gov/sites/entrez?Db=gene&Cmd=ShowDetailView&TermToSearch=23677", Retrieved Aug. 16, 2011, from http://www.ncbi.nlm.nih.gov/sites/entrez?Db=gene&Cmd=ShowDetailView&TermToSearch=23677, Aug. 16, 2011.

OMIM, "OMIM entry#607284: LSM4 Protein; LSM4", Retrieved Aug. 16, 2011, from http://omim.org/entry/607284, Jul. 29, 2003, 1-4.

OMIM, "OMIM: Inositol Polyphosphate-5-Phosphatase, 145-KD; INPP5D. Retrieved Aug. 16, 2011, from http://omim.org/entry/601582?search=INPP5D", Retrieved Aug. 16, 2011, from http://omim.org/entry/601582?search=INPP5D, Oct. 26, 2010.

Roberts, et al., "Effects of Arachidonic Acid Supplementatoin on Training Adaptations in Resistance-Trained Males", Journal of the International Society of Sports Nutrition, 2007, 4:21, doi:10/1186/1550-2783-4-21.

Sahelian, "Muscular Dystrophy Natural Treatment Options", Available from http://www.raysahelian.com/musculardystrophy.com.

Sciencedaily, "Creatine Supplement May Help People with Muscular Dystrophies", Jan. 31, 2007, Center for the advancement of Health.

Sutter, et al., "Extensive and Breed-Specific Linkage disequilibrium in Canis Familiaris", Genome Res. 2004 14: 2388-2396, 2004, 2388-2396.

Tang, et al., "A Histone Deacetylase 4/Myogenin Positive Feedback Loop Coordinates Denervation-dependent Gene Induction and Suppression", Molecular Biology of the Cell, vol. 20, 1120-1131, Feb. 15, 2009.

Zhu, et al., "Single Nucleotide polymorphisms refine QTL intervals for hip joint laxity in dogs", Animal Genetics, Blackwell Scientific Publications, London, GB, vol. 39, No. 2, Apr. 1, 2008, 141-146.

\* cited by examiner

GENETIC TEST

FIELD OF THE INVENTION

The invention relates to a method of determining the susceptibility of a dog to, or the likelihood that a dog is protected from, hip dysplasia.

BACKGROUND OF THE INVENTION

Canine hip dysplasia (CHD) is a polygenic disease of abnormal hip joint formation. It is common in many dog breeds, particularly the larger breeds such as the Labrador, Newfoundland, German Shepherd, Golden Retriever, Rottweiler and Mastiff and also some smaller breeds, such as Spaniels and Pugs. Hip dysplasia is one of the most studied veterinary conditions in dogs and is the most common single cause of arthritis of the hip in canine animals.

Canine hip dysplasia can cause mild to extreme pain as well as mobility problems. Dogs exhibit signs of stiffness or soreness after rising from rest, reluctance to exercise, bunny hopping or other abnormal gait, tenderness, pain, reluctance to stand on rear legs, jump up or climb stairs, subluxation or dislocation of the hip joint or wasting away of the muscle mass in the hip area. Radiographs (X-rays) often confirm the presence of hip dysplasia, but radiographic features may not be present until two years of age in some dogs.

Diagnosis is currently with x-rays or hip score tests. If done at too young an age, the signs may not be revealed.

The causes of hip dysplasia are considered heritable, although environment may also pay a role. Previously, some genetic variants have been associated with the disease but no specific causative mutations have been identified.

It would be of considerable benefit for a non-invasive genetic test to be available.

SUMMARY OF THE INVENTION

The inventors have determined that hip dysplasia in dogs is orthologous with congenital muscular dystrophy. Mutations linked to canine hip dysplasia were found and a model predicting disease was generated. The model is extremely successful at predicting hip dysplasia score, achieving an accuracy of 94% (which is unusually high for a genetic test). Other models can be used.

The inventors have discovered a number of polymorphisms in the genome of the dog that are associated with susceptibility to hip dysplasia. They have also discovered polymorphisms in the genome of the dog that are associated with protection from hip dysplasia. The discovery of these polymorphisms provides the basis for a test to predict the susceptibility of a dog to, or the likelihood of protection of a dog from, hip dysplasia by screening for the polymorphisms. The predictive power of the test can be magnified using models that involve combining the results of detecting one or more of the defined polymorphisms.

The invention thus enables dogs to be identified which are at risk of developing, or are not protected from, hip dysplasia. Once the susceptibility of a dog to hip dysplasia has been identified, it may be possible to identify suitable preventative measures for that dog. Furthermore, dogs that are identified as not having mutations associated with susceptibility to hip dysplasia or having a genetic make-up which is protective from hip dysplasia are preferred for use in breeding programs with the aim of producing dogs that are less likely to suffer from hip dysplasia.

Thus, the invention provides, as a first aspect a method of testing a dog to determine the susceptibility to hip dysplasia by identifying a mutation known to be associated with muscular dystrophy in humans (i.e. an orthologue). In particular, the first aspect of the invention relates to a method of testing a dog to determine the susceptibility of the dog to hip dysplasia, or the likelihood that the dog is protected from hip dysplasia, comprising detecting in a sample the presence or absence in the genome of the dog, one or more mutations in any one or more of the following genes:

| Gene | Location |
| --- | --- |
| Laminin alpha 2 subunit Fragment | Chromosome 1: 70,790,697-71,150,490 |
| LSM4 homolog, U6 small nuclear RNA associated | Chromosome 20: 47,714,464-47,721,805 |
| Collagen, type VI, alpha 3 | Chromosome 25: 50,995,186-51,063,665 |
| CDP-diacylglycerol synthase (phosphatidate cytidylyltransferase) 1 | Chromosome 32: 11,331,461-11,375,767 |
| inositol polyphosphate-5-phosphatase | Chromosome 25: 47,629,437-47,731,096 |
| SH3-domain binding protein 4 | Chromosome 25: 49,142,306-49,155,351 |
| histone deacetylase 4 | Chromosome 25: 52,342,017-52,443,682 |
| Leucine rich repeat protein 1 | Chromosome 8: 29,236,409-29,246,995 |
| v-ski sarcoma viral oncogene homolog | Chromosome 5: 60,146,103-60,213,750 |
| prostaglandin D2 | Chromosome 8: 31,485,692-31,494,066 |

The invention also provides:
a database comprising information relating to one or more polymorphisms as defined herein and their association with the susceptibility of a dog to hip dysplasia;
a method of determining the susceptibility of a dog to hip dysplasia, comprising:
  (a) inputting to a computer system data concerning the presence or absence in the genome of the dog of one or more polymorphisms as defined herein;
  (b) comparing the data to a computer database, which database comprises information relating to one or more polymorphisms as defined herein and their association with the susceptibility of a dog to hip dysplasia; and
  (c) determining on the basis of the comparison the susceptibility of the dog to hip dysplasia;
a computer program comprising program code means that, when executed on a computer system, instruct the computer system to perform a method of the invention;
a computer storage medium comprising the computer program of the invention and the database of the invention;
a computer system arranged to perform a method of the invention comprising:
  (a) means for receiving data concerning the presence or absence in the genome of the dog of a polymorphism as defined herein;
  (b) a database comprising information relating to one or more polymorphisms as defined herein and their association with the susceptibility of a dog to hip dysplasia;
  (c) a module for comparing the data with the database; and
  (d) means for determining on the basis of said comparison the susceptibility of the dog to hip dysplasia;

a method of determining the susceptibility of a dog to hip dysplasia, comprising detecting in a sample the presence or absence in the genome of the dog of one or more polymorphisms selected from the polymorphisms as defined herein;

use of one or more polymorphisms selected from the polymorphisms as defined herein for determining the susceptibility of a dog to hip dysplasia; and a method of selecting a dog for producing offspring likely to be protected from hip dysplasia:
  determining whether the genome of a candidate first dog comprises one or more polymorphisms indicative of susceptibility to hip dysplasia to the method of the invention and thereby determining whether the candidate first dog is suitable for producing offspring likely to be protected from hip dysplasia;
  optionally, determining whether the genome of a second dog of the opposite sex to the first dog comprises one or more polymorphisms indicative of susceptibility to hip dysplasia according to the method of the invention; and
  optionally, mating the first dog with the second dog in order to produce offspring likely to be protected from hip dysplasia.

DETAILED DESCRIPTION OF THE INVENTION

Identifying Susceptibility to or Protection from Hip Dysplasia

The present invention, according to a first aspect, provides a method of testing a dog to determine the susceptibility or the likelihood of protection of the dog to/from hip dysplasia. The susceptibility is the risk of developing hip dysplasia. A dog which suffers from or is susceptible to hip dysplasia may be able to be identified, although signs may not be revealed until at least 2 years of age. Such identification includes X-ray identification (according to common general knowledge), a hip score test, canine breed, family history, sex or breed. A definition of CHD can be by the hip joint laxity measured as Norberg Angle or distraction index and hip scores according to the Federation Cynologique International (FCI) for CHD grading. The risk may be determined by an animal professional, such as a veterinarian or a veterinarian nurse.

Polymorphisms and Indication of Susceptibility to, or Protection from, Hip Dysplasia.

The inventors have discovered a number of chromosomes in the genome of the dog that are associated with susceptibility to hip dysplasia. The present invention therefore relates to a method of determining the susceptibility of a dog to hip dysplasia or the likelihood of protection from hip dysplasia using one or more polymorphic markers on these chromosomes.

The first aspect of the present invention therefore also provides a method of testing a dog to determine the susceptibility (or protection) of the dog to hip dysplasia where the mutation is any one or more of the following single nucleotide polymorphisms in the stated genes:

| Laminin alpha 2 subunit Fragment | | | | |
|---|---|---|---|---|
| SNP | chr | Loc | bases | Risk allele |
| 1_70997779 | 1 | 70997779 | AT | T |
| 1_70938018 | 1 | 70938018 | TA | A |
| 1_70976949 | 1 | 70976949 | AT | A |
| 1_70793904 | 1 | 70793904 | AG | A |
| 1_70931272 | 1 | 70931272 | CA | C |
| 1_71093063 | 1 | 71093063 | CT | T |
| 1_71058059 | 1 | 71058059 | CT | T |

| LSM4 homolog, U6 small nuclear RNA associated | | | | |
|---|---|---|---|---|
| SNP | chr | Loc | bases | Risk allele |
| 20_47714388 | 20 | 47714388 | GA | G |
| 20_48071192 | 20 | 48071192 | GA | G |
| 20_47714336 | 20 | 47714336 | GT | G |
| 20_47714335 | 20 | 47714335 | GT | G |
| 20_47716669 | 20 | 47716669 | GA | G |

| Collagen, type VI, alpha 3 | | | | |
|---|---|---|---|---|
| SNP | chr | loc | bases | Risk allele |
| 25_51040259 | 25 | 51040259 | AG | G |
| 25_51046607 | 25 | 51046607 | AG | A |
| 25_51031100 | 25 | 51031100 | AG | G |
| 25_51006290 | 25 | 51006290 | AG | G |
| 25_51028472 | 25 | 51028472 | GC | G |
| 25_51030165 | 25 | 51030165 | AG | G |
| 25_51063452 | 25 | 51063452 | AG | G |
| 25_51034440 | 25 | 51034440 | CT | C |
| 25_51023068 | 25 | 51023068 | CT | T |
| 25_51038074 | 25 | 51038074 | CT | C |
| 25_51029326 | 25 | 51029326 | AG | A |
| 25_51042357 | 25 | 51042357 | CT | T |
| 25_51040505 | 25 | 51040505 | AG | A |

| CDP-diacylglycerol synthase (phosphatidate cytidylyltransferase) 1 | | | | |
|---|---|---|---|---|
| SNP | chr | loc | bases | Risk allele |
| 32_11331413 | 32 | 11331413 | AC | A |
| 32_11360412 | 32 | 11360412 | TG | T |
| 32_11362156 | 32 | 11362156 | AG | G |
| 32_11366128 | 32 | 11366128 | CT | C |
| 32_11376468 | 32 | 11376468 | TG | T |
| 32_11376837 | 32 | 11376837 | TG | G |
| 32_12479099 | 32 | 12479099 | AG | A |
| 32_11365955 | 32 | 11365955 | AG | G |
| 32_11366052 | 32 | 11366052 | CT | T |
| 32_11371139 | 32 | 11371139 | TG | G |
| 32_11365924 | 32 | 11365924 | CT | T |
| 32_11360206 | 32 | 11360206 | TG | T |
| 32_11378017 | 32 | 11378017 | AG | A | inositol polyphosphate-5-phosphatase

| SNP | chr | loc | bases | Risk allele |
|---|---|---|---|---|
| 25_47684060 | 25 | 47684060 | TC | C |
| 25_47664131 | 25 | 47664131 | CT | C |
| 25_47684091 | 25 | 47684091 | TC | C |
| 25_47685188 | 25 | 47685188 | CT | T |
| 25_47666842 | 25 | 47666842 | AG | G |

SH3-domain binding protein 4

| SNP | chr | loc | bases | Risk allele |
|---|---|---|---|---|
| 25_49142073 | 25 | 49142073 | CT | T | histone deacetylase 4

| SNP | chr | loc | bases | Risk allele |
|---|---|---|---|---|
| 25_52402027 | 25 | 52402027 | CT | T |

Leucine rich repeat protein 1

| SNP | chr | loc | bases | Risk allele |
|---|---|---|---|---|
| 8_29247021 | 8 | 29247021 | TC | T | v-ski sarcoma viral oncogene homolog

| SNP | chr | loc | bases | Risk allele |
|---|---|---|---|---|
| 5_60210935 | 5 | 60210935 | AC | C | prostaglandin D2

| SNP | chr | loc | bases | Risk allele |
|---|---|---|---|---|
| 8_31494277 | 8 | 31494277 | CT | C |
| 8_31494760 | 8 | 31494760 | CA | C |

(b) or is one or more polymorphisms in linkage disequilibrium with any one or more of the polymorphisms.

The susceptibility of the dog is highest when the risk allele is identified (or a polymorphism in linkage disequilibrium). The likelihood of protection may be highest when the risk allele is not identified.

The phrase "detecting the presence or absence of a polymorphism" typically means determining whether a polymorphism is present in the genome of the dog. Polymorphisms include Single Nucleotide Polymorphisms (SNPs), microsatellite or repeat polymorphisms, insertion polymorphisms and deletion polymorphisms. Preferably the polymorphism is a SNP. The polymorphism may be the risk allele listed herein. Detecting the presence or absence of a SNP means genotyping the SNP or typing the nucleotide(s) present in the genome of the dog for the SNP. Typically, the nucleotide present at the same position on both homologous chromosomes will be determined. In other words, one or both alleles are genotyped and the identities of one or both alleles are determined based on the genotyping. A dog may be determined to be homozygous for a first allele, heterozygous or homozygous for a second allele of the SNP. When the polymorphism is a microsatellite or repeat sequence, typically the method will involve determining the number of repeats.

Determining a phenotype of an individual, such as the susceptibility of the individual to, or the protection of the individual from, a disease or condition, is not limited to the detection of a polymorphism that is causal for the disease or condition. In genetic mapping studies, genetic variation at a set of marker loci in a sample of individuals is tested for association with a given phenotype. If such an association is found between a particular marker locus and the phenotype, it suggests that either the variation at that marker locus affects the phenotype of interest, or that the variation at that marker locus is in linkage disequilibrium with the true phenotype-related locus, which was not genotyped. In the case of a group of polymorphisms that are in linkage disequilibrium with each other, knowledge of the existence of all such polymorphisms in a particular individual generally provides redundant information. Thus, when determining whether the genome of a dog comprises one or more polymorphisms indicative of susceptibility to, or protection from, liver copper accumulation or to copper-associated liver disease, it is necessary to detect only one polymorphism of such a group of polymorphisms.

As a result of linkage disequilibrium, a polymorphism that is not a functional susceptibility/protective polymorphism, but is in linkage disequilibrium with a functional polymorphism, may act as a marker indicating the presence of the functional polymorphism. A polymorphism that is in linkage disequilibrium with a polymorphism of the invention is indicative of susceptibility to, or protection from, hip dysplasia.

Accordingly, any one of the polymorphic positions as defined herein may be typed directly, in other words by determining the nucleotide present at that position, or indirectly, for example by determining the nucleotide present at another polymorphic position that is in linkage disequilibrium with said polymorphic position.

Linkage disequilibrium is the non-random gametic association of alleles at different loci in a population. Polymorphisms that have a tendency to be inherited together instead of being inherited independently by random assortment are in linkage disequilibrium. Polymorphisms are randomly assorted or inherited independently of each other if the frequency of the two polymorphisms together is the product of the frequencies of the two polymorphisms individually. For example, if two polymorphisms at different polymorphic sites are present in 50% of the chromosomes in a population, then they would be said to assort randomly if the two alleles are present together on 25% of the chromosomes in the population. A higher percentage would mean that the two alleles are linked. It follows that a first polymorphism is in linkage disequilibrium with a second polymorphism if the frequency of the two polymorphisms together is greater than the product of the frequencies of the two polymorphisms individually in a population. Preferably, a first polymorphism is in linkage disequilibrium with a second polymorphism if the frequency of the two polymorphisms together is more that 10% greater, for example more than 30%, more than 50% or more than 70% greater, than the product of the frequencies of the two polymorphisms individually.

Research has shown that linkage disequilibrium is extensive in dogs (Extensive and breed-specific linkage disequilibrium in *Canis familiaris*, Sutter et al., Genome Research 14: 2388-2396). Polymorphisms which are in linkage disequilibrium are often in close physical proximity, which is why they are co-inherited. Polymorphisms which are in linkage disequilibrium with the polymorphisms mentioned herein are located on the same chromosome. Polymorphisms which are in linkage disequilibrium in dogs are typically within 5 mb, preferably within 2 mb, within 1 mb, within 700 kb, within 600 kb, within 500 kb, within 400 kb, within 200 kb, within 100 kb, within 50 kb, within 10 kb, within 5 kb, within 1 kb, within 500 bp, within 100 bp, within 50 bp or within 10 bp of the polymorphism.

It is within the capability of the skilled person to use routine techniques to identify polymorphisms that are in linkage disequilibrium with any one of the polymorphic positions as defined herein. Once a potential polymorphism has been selected, the skilled person can readily determine whether this polymorphism, and what version or allele of the polymorphism, is significantly correlated with any of the polymorphisms defined herein.

In more detail, to determine whether a polymorphism is in linkage disequilibrium with any one of the polymorphisms defined herein, the skilled person should genotype the candidate polymorphism and one or more of the polymorphisms defined herein in a panel of dogs. The size of the panel should be adequate enough to achieve a statistically significant result. Typically, samples from at least 100, preferably at least 150 or at least 200, different dogs should be genotyped. The dogs in the panel may be of any breed, but typically will have the same or similar genetic breed background. Once the polymorphisms have been genotyped in the panel of dogs, linkage disequilibrium between one or more pairs of polymorphisms can be measured using any one of a number of readily available statistical packages. An example of a free software package is Haploview (Haploview: analysis and visualisation of LD and haplotype maps, Barrett et al, 2005, Bioinformatics, 21(2): 263-265), downloadable at http://www.broadinstitute.org/haploview/haploview. Another example of software that can be used is PLINK (http://pngu.mgh.harvard.edu/purcell/plink/).

A measure of linkage disequilibrium is D'. A range of 0.5 to 1 for D' is indicative of a pair of polymorphisms being in linkage disequilibrium, with 1 indicating the most significant linkage disequilibrium. Therefore if D' is found to be from 0.5 to 1, preferably from 0.6 to 1, 0.7 to 1, from 0.8 to 1, from 0.85 to 1, from 0.9 to 1, from 0.95 to 1 or most preferably 1, for a candidate polymorphism and a specific polymorphism defined herein, the candidate polymorphism may be said to be predictive of the polymorphism defined herein and will thus indicate susceptibility to or protection from liver copper accumulation. In a preferred method of the invention, a polymorphism that is in linkage disequilibrium with a polymorphism defined herein is within 680 kb and on the same chromosome as the polymorphism defined herein and the calculated measure of linkage disequilibrium between the pair of polymorphisms, D', is greater than or equal to 0.9.

Another measure of linkage disequilibrium is R-squared, where R is the correlation coefficient. R-squared, which is also known as the 'Coefficient of determination', is the fraction of the variance in the genotypes of the first polymorphism which is accounted for in the genotypes of the second polymorphism. Therefore an R-squared of 0.5 for a candidate polymorphism and a specific polymorphism defined herein would mean that the candidate polymorphism accounts for 50% of the variance in the specific polymorphism. R-squared is producible from standard statistical packages such as Haploview. Typically, an R-squared of 0.25 or greater (R of >0.5 or <−0.5) is considered a large correlation. Therefore if R-squared is found to be 0.5 or more, preferably 0.75 or more, 0.8 or more, 0.85 or more, 0.9 or more, or 0.95 or more for a candidate polymorphism and a specific polymorphism defined herein, the candidate polymorphism may be said to be predictive of the polymorphism defined herein and will thus indicate susceptibility to or protection from liver copper accumulation. In a preferred method of the invention, a polymorphism that is in linkage disequilibrium with a polymorphism defined herein is within 680 kb and on the same chromosome as the polymorphism defined herein and the calculated measure of linkage disequilibrium between the pair of polymorphisms, R-squared, is greater than or equal to 0.5.

It is also possible to build a haplotype of polymorphisms in LD with the polymorphisms of the invention. Even if one or more polymorphisms are individually only weakly in LD with the polymorphisms of the invention, they may be in strong LD if they are used in combination. For example, any one polymorphism may have an R-squared value below 0.25. However, two or more mutations individually having an R-squared of below 0.25 may in combination have an R-squared of greater than 0.5. Therefore, these polymorphisms may be used in combination to determine the susceptibility of the dog to, or the likelihood of protection of the dog from, liver copper accumulation.

Therefore, the method of the invention may comprise detecting the presence or absence of two or more polymorphisms in linkage disequilibrium with a polymorphism defined herein, wherein R-squared for each of said two or more polymorphisms individually may be less than or equal to 0.25, but R-squared for the combination of said two or more polymorphisms is greater than or equal to 0.5.

Once a polymorphism has been identified as being in linkage disequilibrium and therefore correlated with a polymorphism defined herein, the skilled person can readily determine which version of the polymorphism, i.e. which allele, is associated with susceptibility to or protection from hip dysplasia. This could be achieved by phenotyping a panel of dogs for hip dysplasia and classifying the dogs in terms of the risk of susceptibility to hip dysplasia. The panel of dogs are then genotyped for the polymorphism of interest. The genotypes are then correlated with the risk of hip dysplasia in order to determine the association of the genotypes with hip dysplasia and thereby determine which allele is associated with susceptibility to or protection from hip dysplasia.

Any number and any combination of mutations may be detected to carry out the invention. Preferably at least two mutations are detected, including the polymorphisms described. Preferably 2 to 5, 3 to 8, 5 to 10 or 8 to 15 polymorphisms are detected. Preferably, the method involves determining the presence or absence of a mutation in the laminin alpha 2 subunit fragment, as herein described, in particular a SNP in this gene as herein described.

The method may also preferably involve determining the presence or absence of a mutation in the collagen type VI, alpha 3 gene herein described, in particular an SNP in this gene as herein described. In particular the method may include determining the presence or absence of a mutation in both the laminin alpha 2 subunit fragment as described herein, optionally one of the SNPs in such a gene herein described and a mutation in the collagen type VI, alpha 3 gene herein described, in particular an SNP in this gene herein described.

The method may involve determining the presence or absence of a mutation in both of these genes, including the SNPs described and one or more of the other genes and/or SNP as herein described, including the following:
  laminin alpha 2 subunit fragment and
  collagen type VI, alpha 3 gene optionally and
  leucine rich repeat protein 2 and/or
  LSM4 homolog, U6 small nuclear RNA associated and/or any other.

Therefore, the DNA of a dog may be typed at the respective positions of
  (i) polymorphism (a); and/or
  (ii) one or more polymorphisms (b).

Typing the nucleotide(s) present in the genome of the dog at a position identified herein may mean that the nucleotide present at this position in a sequence corresponding exactly with the sequence identified is typed. However, it will be understood that the exact sequences presented herein will not necessarily be present in the dog to be tested. Typing the nucleotide present may therefore be at a position identified herein or at an equivalent or corresponding position in the sequence. The term equivalent as used herein therefore means at or at a position corresponding to that identified herein. The sequence and thus the position of the SNP could for example vary because of deletions or additions of nucleotides in the genome of the dog. Those skilled in the art will be able to determine a position that corresponds to or is equivalent to the relevant position in each of SEQ ID NOs: 1 to 226, using for example a computer program such as GAP, BESTFIT, COMPARE, ALIGN, PILEUP or BLAST. The UWGCG Package provides programs including GAP, BESTFIT, COMPARE, ALIGN and PILEUP that can be used to calculate homology or line up sequences (for example used on their default settings). The BLAST algorithm can also be used to compare or line up two sequences, typically on its default settings. Software for performing a BLAST comparison of two sequences is publicly available through the National Center for Biotechnology Information (http://www.ncbi.nlm.nih.gov/). This algorithm is further described below. Similar publicly available tools for the alignment and comparison of sequences may be found on the European Bioinformatics Institute website (http://www.ebi.ac.uk), for example the ALIGN and CLUSTALW programs.

There are a variety of different methods that can be used to determine whether a polymorphism is indicative of either susceptibility to or protection from hip dysplasia. Typically, the candidate polymorphism is compared to a database of polymorphisms and their association with susceptibility to or protection from hip dysplasia. Such a database is generated by phenotyping a panel of dogs for hip dysplasia, for example by liver biopsy, and classifying the dogs for hip dysplasia. The dogs in the panel are also genotyped for a panel of polymorphisms. It is then possible to determine the association of each genotype with hip dysplasia. Determining whether a polymorphism is indicative of either susceptibility to or protection from hip dysplasia is therefore achieved by locating the polymorphism in the database.

Once the presence or absence of the one or more polymorphisms of the invention have been detected in the genome of the dog, whether the dog is protected from, or susceptible to, hip dysplasia is thereby determined. The genotype of each polymorphism alone or in combination with other polymorphisms is indicative of the protection from, or susceptibility of the dog to, hip dysplasia.

If the method comprises testing for the presence or absence of multiple polymorphisms indicative of susceptibility to, or protection from, hip dysplasia, a model may be used that combines the results to provide an overall assessment of the risk or likelihood that the dog will be susceptible to, or protected from, hip dysplasia. Preferably, a stepwise modelling technique is used.

A dog may be tested by a method of the invention at any age, for example from 0 to 12, 0 to 6, 0 to 5, 0 to 4, 0 to 3, 0 to 2 or 0 to 1 years old. Preferably the dog is tested at as young an age as possible, for example within the first year, first 6 months or first 3 months of its life. The dog is preferably tested before hip dysplasia occurs or the dog can be tested by an alternative method. The history of the dog may or may not be known. For example, the dog may be a pup of known parents and the history of the parents with respect to hip dysplasia may be known. Alternatively, the dog may be a stray or a rescued dog with unknown parentage and history.

The dog to be tested by any method of the present invention may be of any breed. The invention provides a method of determining whether the genome of a mixed or crossbred dog, or a mongrel or out-bred dog comprises one or more polymorphisms indicative of protection from, or susceptibility to, hip dysplasia.

In the method of the invention, the dog may be one that is suspected of being susceptible to hip dysplasia. Alternatively, the dog may be suspected of being protected from hip dysplasia.

Typically the dog will have genetic inheritance of a breed selected from Labrador Retriever, German Shepherd, Rottweiler, Golden Retriever, Chow Chow, Boxer, Retriever, Pit Bull, Australian Shepherd, Border Collie, English Bulldog, Beagle, Husky, Pug, Akita, Shih Tzu, Mastiff, Saint Bernard, American Bulldog, Collie, Great Dane, Dalmatian, Basset Hound, Doberman Pinscher, American Cocker Spaniel, Terrier, Siberian Husky or is related to or bred from such a breed. The dog may be a mixed or crossbred dog, or a mongrel or out-bred dog. The dog may have at least 25%, at least 50%, or at least 100% of its genome inherited from any pure breed or more preferably from any of the breeds described herein. The dog may be a pure-bred. In one embodiment of the invention, one or both parents of the dog to be tested are or were pure-bred dogs. In another embodiment, one or more grandparents are or were pure-bred dogs. One, two, three or all four of the grandparents of the dog that is tested may be or may have been pure-bred dogs.

The genetic breed background of a dog may be determined by assessing the allelic frequencies of genetic markers, for example SNPs or microsatellites. The combinations of allelic frequencies of different SNPs or microsatellites in a dog provide a signature that allows the breed of a dog or the breeds that make up a mixed breed dog to be determined. Such a genetic test may be a commercially available test. Alternatively, the dog may not need to be tested for the genetic inheritance of a particular breed because it is suspected of having a particular breed inheritance for example by the dog owner or veterinarian. This could be for example because of knowledge of the dog's ancestry or because of its appearance.

The predictive test of the invention may be carried out in conjunction with one or more other predictive or diagnostic tests such as determining the genetic breed background/inheritance of the dog or susceptibility to one or more other diseases.

Detection of Polymorphisms

The detection of polymorphisms according to the invention may comprise contacting a polynucleotide or protein in a sample from the dog with a specific binding agent for a polymorphism and determining whether the agent binds to the polynucleotide or protein, wherein binding of the agent indicates the presence of the polymorphism, and lack of binding of the agent indicates the absence of the polymorphism.

The method is generally carried out in vitro on a sample from the dog, where the sample contains DNA from the dog. The sample typically comprises a body fluid and/or cells of the dog and may, for example, be obtained using a swab, such as a mouth swab. The sample may be a blood, urine, saliva, skin, cheek cell or hair root sample. The sample is typically processed before the method is carried out, for example DNA extraction may be carried out. The polynucleotide or protein in the sample may be cleaved either physically or chemically, for example using a suitable enzyme. In one embodiment the part of polynucleotide in the sample is copied or amplified, for example by cloning or using a PCR based method prior to detecting the polymorphism.

In the present invention, any one or more methods may comprise determining the presence or absence of one or more polymorphisms in the dog. The polymorphism is typically detected by directly determining the presence of the polymorphic sequence in a polynucleotide or protein of the dog. Such a polynucleotide is typically genomic DNA, mRNA or cDNA. The polymorphism may be detected by any suitable method such as those mentioned below.

A specific binding agent is an agent that binds with preferential or high affinity to the protein or polypeptide having the polymorphism but does not bind or binds with only low affinity to other polypeptides or proteins. The specific binding agent may be a probe or primer. The probe may be a protein (such as an antibody) or an oligonucleotide. The probe may be labelled or may be capable of being labelled indirectly. The binding of the probe to the polynucleotide or protein may be used to immobilise either the probe or the polynucleotide or protein.

Generally in the method, a polymorphism can be detected by determining the binding of the agent to the polymorphic polynucleotide or protein of the dog. However in one embodiment the agent is also able to bind the corresponding wild-type sequence, for example by binding the nucleotides or amino acids which flank the variant position, although the manner of binding to the wild-type sequence will be detectably different to the binding of a polynucleotide or protein containing the polymorphism.

The method may be based on an oligonucleotide ligation assay in which two oligonucleotide probes are used. These probes bind to adjacent areas on the polynucleotide that contains the polymorphism, allowing after binding the two probes to be ligated together by an appropriate ligase enzyme. However the presence of a single mismatch within one of the probes may disrupt binding and ligation. Thus ligated probes will only occur with a polynucleotide that contains the polymorphism, and therefore the detection of the ligated product may be used to determine the presence of the polymorphism.

In one embodiment the probe is used in a heteroduplex analysis based system. In such a system when the probe is bound to a polynucleotide sequence containing the polymorphism it forms a heteroduplex at the site where the polymorphism occurs and hence does not form a double strand structure. Such a heteroduplex structure can be detected by the use of a single or double strand specific enzyme. Typically the probe is an RNA probe, the heteroduplex region is cleaved using RNAase H and the polymorphism is detected by detecting the cleavage products.

The method may be based on fluorescent chemical cleavage mismatch analysis which is described for example in PCR Methods and Applications 3, 268-71 (1994) and Proc. Natl. Acad. Sci. 85, 4397-4401 (1998).

In one embodiment a PCR primer is used that primes a PCR reaction only if it binds a polynucleotide containing the polymorphism, for example a sequence-specific PCR system, and the presence of the polymorphism may be determined by detecting the PCR product. Preferably the region of the primer that is complementary to the polymorphism is at or near the 3' end of the primer. The presence of the polymorphism may be determined using a fluorescent dye and quenching agent-based PCR assay such as the Taqman PCR detection system.

The specific binding agent may be capable of specifically binding the amino acid sequence encoded by a polymorphic sequence. For example, the agent may be an antibody or antibody fragment. The detection method may be based on an ELISA system. The method may be an RFLP based system. This can be used if the presence of the polymorphism in the polynucleotide creates or destroys a restriction site that is recognised by a restriction enzyme.

The presence of the polymorphism may be determined based on the change that the presence of the polymorphism makes to the mobility of the polynucleotide or protein during gel electrophoresis. In the case of a polynucleotide, single-stranded conformation polymorphism (SSCP) or denaturing gradient gel electrophoresis (DDGE) analysis may be used. In another method of detecting the polymorphism, a polynucleotide comprising the polymorphic region is sequenced across the region that contains the polymorphism to determine the presence of the polymorphism.

The presence of the polymorphism may be detected by means of fluorescence resonance energy transfer (FRET). In particular, the polymorphism may be detected by means of a dual hybridisation probe system. This method involves the use of two oligonucleotide probes that are located close to each other and that are complementary to an internal segment of a target polynucleotide of interest, where each of the two probes is labelled with a fluorophore. Any suitable fluorescent label or dye may be used as the fluorophore, such that the emission wavelength of the fluorophore on one probe (the donor) overlaps the excitation wavelength of the fluorophore on the second probe (the acceptor). A typical donor fluorophore is fluorescein (FAM), and typical acceptor fluorophores include Texas red, rhodamine, LC-640, LC-705 and cyanine 5 (Cy5).

In order for fluorescence resonance energy transfer to take place, the two fluorophores need to come into close proximity on hybridisation of both probes to the target. When the donor fluorophore is excited with an appropriate wavelength of light, the emission spectrum energy is transferred to the fluorophore on the acceptor probe resulting in its fluorescence. Therefore, detection of this wavelength of light, during excitation at the wavelength appropriate for the donor fluorophore, indicates hybridisation and close association of the fluorophores on the two probes. Each probe may be labelled with a fluorophore at one end such that the probe located upstream (5') is labelled at its 3' end, and the probe located downstream (3') is labelled at its 5' end. The gap between the two probes when bound to the target sequence may be from 1 to 20 nucleotides, preferably from 1 to 17 nucleotides, more preferably from 1 to 10 nucleotides, such as a gap of 1, 2, 4, 6, 8 or 10 nucleotides.

The first of the two probes may be designed to bind to a conserved sequence of the gene adjacent to a polymorphism and the second probe may be designed to bind to a region including one or more polymorphisms. Polymorphisms within the sequence of the gene targeted by the second probe can be detected by measuring the change in melting temperature caused by the resulting base mismatches. The extent of the change in the melting temperature will be dependent on the number and base types involved in the nucleotide polymorphisms.

Polymorphism typing may also be performed using a primer extension technique. In this technique, the target region surrounding the polymorphic site is copied or amplified for example using PCR. A single base sequencing reaction is then performed using a primer that anneals one base away from the polymorphic site (allele-specific nucleotide incorporation). The primer extension product is then detected to determine the nucleotide present at the polymorphic site. There are several ways in which the extension product can be detected. In one detection method for example, fluorescently labelled dideoxynucleotide terminators are used to stop the extension reaction at the polymorphic site. Alternatively, mass-modified dideoxynucleotide terminators are used and the primer extension products are detected using mass spectrometry. By specifically labelling one or more of the terminators, the sequence of the extended primer, and hence the nucleotide present at the polymorphic site can be deduced. More than one reaction product can be analysed per reaction and consequently the nucleotide present on both homologous chromosomes can be determined if more than one terminator is specifically labelled.

The invention further provides primers or probes that may be used in the detection of any of the polymorphisms defined herein for use in the prediction of susceptibility to or protection from liver copper accumulation. Polynucleotides of the invention may also be used as primers for primer extension reactions to detect the SNPs defined herein.

Such primers, probes and other polynucleotide fragments will preferably be at least 10, preferably at least 15 or at least 20, for example at least 25, at least 30 or at least 40 nucleotides in length. They will typically be up to 40, 50, 60, 70, 100 or 150 nucleotides in length. Probes and fragments can be longer than 150 nucleotides in length, for example up to 200, 300, 400, 500, 600, 700 nucleotides in length, or even up to a few nucleotides, such as five or ten nucleotides, short of a full length polynucleotide sequence of the invention.

Primers and probes for genotyping the polymorphisms of the invention may be designed using any suitable design software known in the art using the sequences in Tables 4, 5, 6, 8, 18 and 20. Homologues of these polynucleotide sequences would also be suitable for designing primers and probes. Such homologues typically have at least 70% homology, preferably at least 80, 90%, 95%, 97% or 99% homology, for example over a region of at least 15, 20, 30, 100 more contiguous nucleotides. The homology may be calculated on the basis of nucleotide identity (sometimes referred to as "hard homology").

For example the UWGCG Package provides the BEST-FIT program that can be used to calculate homology (for example used on its default settings) (Devereux et at (1984) *Nucleic Acids Research* 12, p 387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et at (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as default a word length (W) of 11, the BLOSUM62 scoring matrix (see Henikoff and Henikoff (1992) *Proc. Natl. Acad. Sci. USA* 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by at least 1, 2, 5, 10, 20 or more mutations, which may be substitutions, deletions or insertions of nucleotides The polynucleotides of the invention such as primers or probes may be present in an isolated or substantially purified form. They may be mixed with carriers or diluents that will not interfere with their intended use and still be regarded as substantially isolated. They may also be in a substantially purified form, in which case they will generally comprise at least 90%, e.g. at least 95%, 98% or 99%, of polynucleotides of the preparation.

Detector Antibodies

A detector antibody is an antibody that is specific for one polymorphism but does not bind to any other polymorphism as described herein. Detector antibodies are for example useful in purification, isolation or screening methods involving immunoprecipitation techniques.

Antibodies may be raised against specific epitopes of the polypeptides of the invention. An antibody, or other compound, "specifically binds" to a polypeptide when it binds with preferential or high affinity to the protein for which it is specific but does substantially bind not bind or binds with only low affinity to other polypeptides. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

For the purposes of this invention, the term "antibody", unless specified to the contrary, includes fragments that bind a polypeptide of the invention. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies.

Antibodies may be used in a method for detecting polypeptides of the invention in a biological sample (such as any such sample mentioned herein), which method comprises:

I providing an antibody of the invention;

II incubating a biological sample with said antibody under conditions which allow for the formation of an antibody-antigen complex; and III determining whether antibody-antigen complex comprising said antibody is formed.

Antibodies of the invention can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising an antibody in a host animal against the whole polypeptide or a fragment thereof, for example an antigenic epitope thereof, hereinafter the "immunogen". The fragment may be any of the fragments mentioned herein (typically at least 10 or at least 15 amino acids long).

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein (1975) Nature 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat, mouse, guinea pig, chicken, sheep or horse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Detection Kit

The invention also provides a kit that comprises means for typing one or more of the polymorphisms defined herein. In particular, such means may include a specific binding agent, probe, primer, pair or combination of primers, or antibody, including an antibody fragment, as defined herein which is capable of detecting or aiding detection of the polymorphisms defined herein. The primer or pair or combination of primers may be sequence specific primers that only cause PCR amplification of a polynucleotide sequence comprising the polymorphism to be detected, as discussed herein. The primer or pair of primers may alternatively not be specific for the polymorphic nucleotide, but may be specific for the region upstream (5') and/or downstream (3'). These primers allow the region encompassing the polymorphic nucleotide to be copied. A kit suitable for use in the primer-extension technique may specifically include labelled dideoxynucleotide triphosphates (ddNTPs). These may for example be fluorescently labelled or mass modified to enable detection of the extension product and consequently determination of the nucleotide present at the polymorphic position.

The kit may also comprise a specific binding agent, probe, primer, pair or combination of primers, or antibody that is capable of detecting the absence of the polymorphism. The kit may further comprise buffers or aqueous solutions.

The kit may additionally comprise one or more other reagents or instruments that enable any of the embodiments of the method mentioned above to be carried out. Such reagents or instruments may include one or more of the following: a means to detect the binding of the agent to the polymorphism, a detectable label such as a fluorescent label, an enzyme able to act on a polynucleotide, typically a polymerase, restriction enzyme, ligase, RNAse H or an enzyme which can attach a label to a polynucleotide, suitable buffer(s) or aqueous solutions for enzyme reagents, PCR primers which bind to regions flanking the polymorphism as discussed herein, a positive and/or negative control, a gel electrophoresis apparatus, a means to isolate DNA from sample, a means to obtain a sample from the individual, such as swab or an instrument comprising a needle, or a support comprising wells on which detection reactions can be carried out. The kit may be, or include, an array such as a polynucleotide array comprising the specific binding agent, preferably a probe, of the invention. The kit typically includes a set of instructions for using the kit.

Bioinformatics

The sequences of the polymorphisms may be stored in an electronic format, for example in a computer database. Accordingly, the invention provides a database comprising information relating to one or more mutations and/or polymorphisms according to the first aspect of the invention.

A database as described herein may be used to determine whether the genome of a dog comprises one or more polymorphisms indicative of protection from, or susceptibility to, hip dysplasia. Such a determination may be carried out by electronic means, for example by using a computer system (such as a PC).

Typically, the determination of whether the genome of a dog comprises one or more polymorphisms indicative of susceptibility to or protection from hip dysplasia is carried out by inputting to a computer system genetic data from the dog to a computer system; comparing the genetic data to a database as defined herein; and on the basis of this comparison, determining whether the genome of a dog comprises one or more polymorphisms indicative of susceptibility to, or protection from, hip dysplasia.

The invention also provides a computer program comprising program code means for performing all the steps of a method of the invention when said program is run on a computer. Also provided is a computer program product comprising program code means stored on a computer readable medium for performing a method of the invention when said program is run on a computer. A computer program product comprising program code means on a carrier wave that, when executed on a computer system, instruct the computer system to perform a method of the invention is additionally provided.

The invention also provides an apparatus arranged to perform a method according to the invention. The apparatus typically comprises a computer system, such as a PC. In one embodiment, the computer system comprises: means for receiving genetic data from the dog; a module for comparing the data with a database comprising information relating to polymorphisms; and means for determining on the basis of said comparison whether the genome of a dog comprises one or more polymorphisms indicative of protection of a dog from, or susceptibility of a dog to, hip dysplasia.

Breeding Tool

Breeding value is defined as the value of an individual as a parent. In order to reduce the incidence of hip dysplasia it is advantageous to select dogs for breeding that are protected from, or are not susceptible to, hip dysplasia. This problem is solved by the use of polymorphisms that can be used to determine whether a dog is protected from, or not susceptible to, hip dysplasia in order to inform breeding.

Accordingly, the invention provides a method of selecting a dog for producing offspring protected from hip dysplasia comprising determining whether the genome of a dog comprises one or more polymorphisms indicative of protection from hip dysplasia by a method of the invention in a candidate first dog; and thereby determining whether the candidate first dog is suitable for producing offspring susceptible to hip dysplasia. The method may further comprise determining whether the genome of a dog comprises one or more polymorphisms indicative of protection from hip dysplasia by a method of the invention in a second dog of the opposite sex to the first dog. If the results are that the first and/or second dog has a genotype indicative of protection from hip dysplasia, the first dog may then be mated with the second dog in order to produce offspring protected from hip dysplasia.

The invention also provides a method of selecting a dog for producing offspring protected from hip dysplasia by making use of the polymorphisms of the invention that are indicative of susceptibility to hip dysplasia. The absence of such polymorphisms in the genome of the dog indicates that the dog is a good candidate for mating. The method of the invention may therefore comprise determining whether the genome of the candidate first dog comprises one or more polymorphisms indicative of susceptibility to hip dysplasia and thereby determining whether the candidate first dog is suitable for producing offspring protected from hip dysplasia.

The candidate first dog and/or second dog may be of any breed. Preferably the candidate first dog and/or second dog has genetic breed inheritance of a breed selected from Labrador Retriever, German Shepherd, Rottweiler, Golden Retriever, Chow Chow, Boxer, Retriever, Pit Bull, Australian Shepherd, Border Collie, English Bulldog, Beagle, Husky, Pug, Akita, Shih Tzu, Mastiff, Saint Bernard, American Bulldog, Collie, Great Dane, Dalmatian, Basset Hound, Doberman Pinscher, American Cocker Spaniel, Terrier, Siberian Husky or is related to or bred from such a breed.

The genetic breed inheritance of a dog may be determined by assessing the allelic frequencies of genetic markers, for example SNPs or microsatellites. The combinations of allelic frequencies of different SNPs or microsatellites in a dog provide a signature that allows the breed of a dog or the breeds that make up a mixed breed dog to be determined. Such a genetic test may be a commercially available test. Alternatively, the dog may not need to be tested for a particular breed inheritance because it is suspected of having a particular breed inheritance for example by the dog owner or veterinarian. This could be for example because of knowledge of the dog's ancestry or because of its appearance.

Most purebred dogs of breeds recognized by all-breed club registries are controlled by "closed studbooks". A studbook is typically the official registry of approved dogs of a given breed kept by, for example, a breed association or kennel club. It is generally termed a "closed" studbook if dogs can only be added if their parents were both registered. Most breeds have closed studbooks, resulting in inbreeding, as genetic diversity cannot be introduced from outside the existing population. In a number of breeds recognized by kennel clubs this has resulted in high incidences of genetic diseases or disorders and other problems such as reduced litter sizes, reduced lifespan and inability to conceive naturally.

In order to avoid the problems associated with inbreeding, it would be advantageous to select dogs for breeding within a particular breed that are more distantly related to each other compared to dogs that are more closely related. Therefore in one aspect of the invention, the genetic breed inheritance of the candidate first dog and of the candidate second dog is determined in order to determine the degree of relatedness of the two dogs. In this aspect of the invention, the term "genetic breed inheritance" relates to the dog's genetic ancestry within a particular breed. The dog's genetic breed inheritance may be determined as described herein. By determining the dogs' genetic inheritance, it is possible to distinguish between dogs within a single breed in order to determine how closely related they are.

Therefore, in one aspect of the invention the degree of relatedness of the candidate first dog and the candidate second dog is determined, which comprises comparing the genetic breed inheritance of the candidate first dog with the candidate second dog of the same breed. Preferably the dogs are purebred dogs. The genetic breed inheritance of each dog may for example be determined by identifying the presence or absence of one or more breed-specific polymorphisms in said dog.

The degree of relatedness may be determined from the number of breed-specific polymorphisms that the dogs have in common. For example, two dogs of the same breed may have from 0 to 100% of the breed-specific polymorphisms tested in common, for example from 10 to 90%, from 20 to 80%, from 30 to 70% or from 40 to 60%. Therefore two dogs may have at least 10%, 20%, 30%, 40%, 50%, 60%, 70%, 80% or 90% of the breed-specific polymorphisms tested in common. The percentage of tested breed-specific polymorphisms in common between two dogs may be used as a measure of their degree of relatedness. In this aspect of the invention, the two dogs would only be mated together if they are sufficiently genetically unrelated. For example, they may only be mated together if they have less than 60%, 50%, 40%, 30% or less than 20% of the breed-specific polymorphisms tested in common.

The invention also provides a method of selecting one or more dogs for breeding with a subject dog, the method comprising:
 (a) determining for a subject dog and for each dog in a test group of two or more dogs of the opposite sex to the subject dog whether the genome comprises one or more polymorphisms indicative of protection from, and/or one or more polymorphisms indicative of susceptibility to, hip dysplasia; and
 (b) selecting one or more dogs from the test group for breeding with the subject dog.

The test group may consist of at least 2, 3, 4, 5, 10, 15, 20, 25, 30, 50, 75, 100 or 200 different dogs, for example from 2 to 100, from 5 to 70 or from 10 to 50 dogs. The dogs are typically selected from the test group on the basis of being protected from hip dysplasia. The dog or dogs selected from the test group may have the same or similar genetic breed inheritance as the subject dog.

As explained above, it is desirable to mate dogs within the same breed that are most genetically unrelated. This is in order to increase or maintain genetic diversity within the breed, and to reduce the likelihood of problems relating to inbreeding arising within the offspring. A further selection of the dogs from the test group may therefore be based on the genetic relatedness of the dogs with the subject dog. Accordingly, the method may further comprise:

(a) comparing the genetic breed inheritance of the subject dog with the genetic breed inheritance of each dog in a test group of two or more dogs of the same breed and of the opposite sex to the subject dog;

(b) determining from the comparison the degree of relatedness between the subject dog and each dog in the test group; and (c) selecting one or more dogs from the test group for breeding with the subject dog.

The dogs may be selected from the test group on the basis of their relatedness to the subject dog (i.e. the dog to be bred from). Preferably the dog or dogs selected from the test group are the most distantly related (i.e. have the lowest degree of relatedness) within the test group of dogs. The genetic breed inheritance of the subject dog and the dogs in the test group may be already known or may be determined e.g. by a commercially available breed test.

The invention thus provides a method of recommending one or more suitable dogs for breeding with a subject dog. The recommendation may be made to the subject dog's owner or carer, a veterinarian, dog breeder, kennel club or breed registry.

The invention also relates to a method of breeding dogs, wherein the protection from, or susceptibility to, hip dysplasia of at least two dogs of the opposite sex is determined, optionally within the same breed, before breeding them together.

The protection from, or susceptibility to, hip dysplasia of a dog may be stored in an electronic format, for example in a computer database. Accordingly, the invention provides a database comprising information relating to the susceptibility to, or protection from, hip dysplasia and sex of one or more dogs. The database may include further information about the dog, for example the dog's genetic breed inheritance, breeding status, age, geographical location, medical history, disease susceptibility or physical characteristics. The database will typically further comprise a unique identifier for each dog, for example the dog's registered name. The database may be accessed remotely, for example using the internet.

All preferred features of each aspect of the invention apply mutatis mutandis to each other.

The invention is illustrated by the following Examples:
Example
1.1 Purpose of Example This example lays out the results from the sequencing project and the subsequent analysis. Following from this it describes the etiology of canine hip dysplasia (CHD) via a combination of minor defects in muscle and variability in growth rates.

By targeting these muscle defects, a higher muscle growth rate and a lower bone growth rate the disease may be reduced in severity or even eliminated. This document lays out the current support for this theory, alternative hypotheses and modes of intervention.

2. The Sequencing Project
2.1 Sample Collection and Phenotyping

Blood samples from a population of unrelated Dutch Labradors were collected. The FCI hip scoring system was used to phenotype the dogs. Dogs of score 'A' were designated as controls and C D or E as cases. Once phylogenetic outliers were removed, 79 phenotyped samples (49 CHD cases and 30 controls) remained.

In some cases DNA levels were too low for sequencing. A whole genome amplification approach was taken, using three parallel reactions and a pooling of the products. Multiple pools were used to reduce the selection for specific areas of the genome. This produced enough DNA for array-capture.

2.2 Illumina 22k Chip Genotyping

The Illumina Infinium chip was used to genotype the samples on approximately 22,000 SNPs. (Illumina, 2007). Regions were identified by association analysis using the PLINK software.

All coding and regulatory elements within the associated regions could have an effect on CHD development. Therefore all genes within the associated regions are considered candidate genes. However, based on the known functions of these genes, a priority set was selected which consisted of genes associated with cartilage of bone development, synthesis or maintenance. This priority set was sequenced in all the samples from the association studies, while the other (non-priority) genes were sequenced in 15 cases and 15 controls. Nine of the 79 samples were of insufficient quality for sequencing, and were replaced by samples positive for CHD from a sample database.

To be able to increase the number of genes for sequencing, an exome sequencing approach was adopted. In this case we chose to sequence only exons, intron/exon boundaries (30 bp) and the intergenic regions flanking both sides of each gene (2×500 bp). To facilitate haplotype analysis, when the gene was smaller than 3 kb, the 5' (upstream) flanking region was increased until this criterion was met.

To minimize the chance of missing unannotated genes or exons not yet in the current dog genome build, the syntenic regions in the human genome were compared and human cDNA sequences from genes in these regions were BLASTed against the dog genome. When the orientation of the human alignment was correspond to the homologous gene in the dog and located within 100 kb of the gene, this alignment was considered a possible unannotated exon. Canine expressed sequence tags (ESTs) were also BLASTed against the dog genome and alignments were added to the non-priority gene set.

2.3 Sequencing Analysis
2.3.1 SNP Mining and Genotype Assignment

Sequencing data was delivered in pileup format. A custom was then used to identify SNPs in the data and extract genotype calls for them.

The custom program performed the following steps:
1. Remove untargetted regions.
   Due to repetitive sequence and innefficiency in the capture methodoloy, untargetted DNA is sequenced. All sequence more than 200 bp from a targetted base was removed from the data set. Sequence with less than 100× total coverage over all samples was also removed.

2. For each location in the genome:
  a. The genotype for each sample is identified, if an allele is present in more than 10% of the sequences and at least 3 sequences it is counted for that sample
  b. If at least one sample has a different genotype to the others the location is considered to be a SNP and the genotypes outputted for that location 2.3.2 Significance Analysis SNPs were assessed for significance using a chi squared test with two degrees of freedom, testing for independence of phenotype and genotype. The experimental power of non-priority regions is reduced; for this reason SNPs were also considered interesting if they had large odds ratios (>6).

Significant (p-value<0.01) SNPs were checked for significance in the Ensembl Variant Effect Predictor (Ensembl). All other identified SNPs were also processed using this tool and SNPs with interesting predicted effects were noted such as splice site mutations, premature or removed stop codons, non-synonymous coding mutations and mutations in the 3-prime UTR.

Tables 1A and 1B shows the genes these SNPs are associated with.

TABLE 1A

Genes with identified significant mutations

| Gene | Location | Mutations | Most significant p-value |
|---|---|---|---|
| Laminin alpha 2 subunit Fragment | Chromosome 1: 70,790,697-71,150,490 | one synonymous coding mutation, one non-synonymous mutation, but less significant. | 1.17E−04 |
| LSM4 homolog, U6 small nuclear RNA associated | Chromosome 20: 47,714,464-47,721,805 | no coding mutations | 2.18E−04 |
| Collagen, type VI, alpha 3 | Chromosome 25: 50,995,186-51,063,665 | six synonymous coding mutations, one splice site mutation | 9.40E−04 |
| CDP-diacylglycerol synthase (phosphatidate cytidylyltransferase) 1 | Chromosome 32: 11,331,461-11,375,767 | one synonymous coding mutation | 1.08E−03 |
| inositol polyphosphate-5-phosphatase | Chromosome 25: 47,629,437-47,731,096 | two synonymous coding mutations | 1.73E−03 |
| SH3-domain binding protein 4 | Chromosome 25: 49,142,306-49,155,351 | one upstream mutation | 1.74E−03 |
| histone deacetylase 4 | Chromosome 25: 52,342,017-52,443,682 | one intronic mutation | 3.23E−03 |
| Leucine rich repeat protein 1 | Chromosome 8: 29,236,409-29,246,995 | one downstream, potentially in UTR | 4.82E−03 |
| v-ski sarcoma viral oncogene homolog | Chromosome 5: 60,146,103-60,213,750 | one non-synonymous coding mutation | 5.24E−03 |
| prostaglandin D2 | Chromosome 8: 31,485,692-31,494,066 | | |

TABLE 1B

Part 2 of Genes with identified significant mutations. Ensembl IDs:

| Ensembl Gene ID | Associated Gene Name | Description |
|---|---|---|
| ENSCAFG00000001106 | LAMA2 | laminin, alpha 2 [Source: HGNC Symbol; Acc: 6482] |
| ENSCAFG00000009166 | CDS1 | CDP-diacylglycerol synthase (phosphatidate cytidylyltransferase) 1 [Source: HGNC Symbol; Acc: 1800] |
| ENSCAFG00000011650 | INPP5D | inositol polyphosphate 5-phosphatase, 145 kDa [Source: HGNC Symbol; Acc: 6079] |
| ENSCAFG00000012014 | SH3BP4 | SH3-domain binding protein 4 [Source: HGNC Symbol; Acc: 10826] |
| ENSCAFG00000012226 | Q9GLN3_CANFA | collagen alpha-3(VI) chain precursor [Source: RefSeq peptide; Acc: NP_001096685] |
| ENSCAFG00000012546 | HDAC4 | histone deacetylase 4 [Source: HGNC Symbol; Acc: 14063] |
| ENSCAFG00000014177 | LRR1 | leucine rich repeat protein 1 [Source: HGNC Symbol; Acc: 19742] |
| ENSCAFG00000014900 | LSM4 | LSM4 homolog, U6 small nuclear RNA associated [Source: RefSeq peptide; Acc: NP_001104275] |
| ENSCAFG00000019387 | SKI | v-ski sarcoma viral oncogene homolog (avian) [Source: HGNC Symbol; Acc: 10896] |
| ENSCAFG00000014692 | PTGDR | prostaglandin D2 receptor |

2.4 Modelling Receptor Chromosome 8: 31,485,692-31,494,066

Significant SNPs were taken forward to a Stepwise modelling in MATLAB. A p-value cut-off of 0.001 was used for adding/removing factors in the process. The modelling process produced a 4 SNP model.

TABLE 2

Stepwise Linear modelling results

| SNP | Co-efficient | Gene |
|---|---|---|
| 1_70997779 | 0.39 | Laminin alpha 2 subunit Fragment |
| 8_29247021 | −0.21 | Leucine rich repeat protein 1 |
| 20_47714388 | −0.25 | LSM4 homolog, U6 small nuclear RNA associated |
| 25_51006290 | 0.38 | Collagen, type VI, alpha 3 |

The odds ratio achieved from the model is not quantifiable because there is 100% NPV at the best cut-off location. We can say the value exceeds 200 though. When a single observation of each binary test statistic (true positive, false positive, true negative, false negative) is added, the estimation of odds ratio is 208 with a 95% confidence interval of 23.75 to 1821.97. The accuracy of the model is 94% (95% C.I of 88%-99%), positive predictive value of 90%, negative predictive value of 100%, sensitivity of 100% and specificity of 83%.

3. Gene Discussion

The following sections discuss the biological relevance and implications of the genes with identified mutations.

mutation could still effect protein function as mutations that do not directly change the protein can still have a significant effect.

Up-regulating alpha 7 integrin in a transgenic mouse model of the disease was able to correct the phenotype. This is thought to work by generating more of another protein complex that binds muscles together, "Enhanced expression of the alpha 7 integrin restored sarcolemmal localization of the alpha 7 1 integrin to laminin-2-deficient myofibers, changed the composition of the muscle extracellular matrix, reduced muscle pathology, maintained muscle strength and function and improved the life expectancy of dy(W/) mice". This suggests that if alpha 7 integrin can be stimulated through nutrition, a potential solution might be reached for this etiological process.

It is also possible that as Laminin is involved in calcium metabolism, the etiology may be partially corrected through nutritionally targeting calcium handling.

The table below shows the mutations detected with p-values and potential for consequence.

The most significant finding was that the synonymous coding mutation does not change amino acid sequence but does sit near a splice site. It is potentially possible that this mutation impacts splice site choice. The principal alternative splice site is 4 bases downstream and would cause a frame-shift being deleterious to protein function. This could be followed up with RNA sequencing. The non-synonymous mutation is in exon 16 changing a serine at codon 716 to and arginine.

| SNP | chr | Loc | bases | chisquared p-value | Consequence | Risk allele |
|---|---|---|---|---|---|---|
| 1_70997779 | 1 | 70997779 | AT | 0.000116946 | SYNONYMOUS_CODING | T |
| 1_70938018 | 1 | 70938018 | TA | 0.000121843 | INTRONIC | A |
| 1_70976949 | 1 | 70976949 | AT | 0.004028234 | INTRONIC | A |
| 1_70793904 | 1 | 70793904 | AG | 0.005463992 | INTRONIC | A |
| 1_70931272 | 1 | 70931272 | CA | 0.007215438 | NON_SYNONYMOUS_CODING | C |
| 1_71093063 | 1 | 71093063 | CT | 0.008791528 | INTRONIC | T |
| 1_71058059 | 1 | 71058059 | CT | 0.009974262 | INTRONIC | T |

Results were shared with an experienced veterinarian and an expert in in vitro models of cartilage disease.

3.1.1 Laminin Alpha 2 Subunit Fragment

Mutations in Laminin could therefore be responsible for the non-ideal growth of the joint.

Mutations in the laminin gene have also been shown to cause 'congenital merosin-deficient muscular dystrophy'. The problem occurs because of a defect in a gene coding a protein that binds muscle fibres together.

The most significant mutation discovered in the gene was a synonymous coding mutation. Synonymous coding mutations are mutations in the sequence effecting a protein but not directly changing the protein sequence. However the

3.1.2 LSM4 Homolog, U6 Small Nuclear RNA Associated

In yeast and *C. elegans*, LSM4 has been associated with growth rate (OMIM, OMIM entry: LSM4 PROTEIN; LSM4, 2003). In meta-studies genes associated with phenotypes such as growth-rate often show orthologous actions in other species. Controlling growth rate is a known method for delaying the development of canine hip dysplasia.

The most significant of the SNPs (20_47714388) is less than 100 bases from the gene and could modulate gene expression. The mutation is at a site that is predicted by the TFSEARCH tool to be required for the binding of the HSF and GATA-1 transcription factors.

| SNP | chr | Loc | bases | chisquared p-value | Consequence | Risk allele |
|---|---|---|---|---|---|---|
| 20_47714388 | 20 | 47714388 | GA | 0.000218115 | UPSTREAM | G |
| 20_48071192 | 20 | 48071192 | GA | 0.000814514 | DOWNSTREAM | G |
| 20_47714336 | 20 | 47714336 | GT | 0.0016715 | UPSTREAM | G |
| 20_47714335 | 20 | 47714335 | GT | 0.003063477 | UPSTREAM | G |
| 20_47716669 | 20 | 47716669 | GA | 0.009898801 | INTRONIC | G |

3.1.3 Collagen, Type VI, Alpha 3

Type 6 collagen is located at the epiphyseal growth plate. Collagen 6A3 (along with Laminin) has also been linked with 'congenital merosin-deficient muscular dystrophy'.

| SNP | chr | loc | bases | chisquared p-value | Consequence | Risk allele |
|---|---|---|---|---|---|---|
| 25_51040259 | 25 | 51040259 | AG | 0.000940494 | SYNONYMOUS_CODING | G |
| 25_51046607 | 25 | 51046607 | AG | 0.001043759 | SYNONYMOUS_CODING | A |
| 25_51031100 | 25 | 51031100 | AG | 0.001347902 | SYNONYMOUS_CODING | G |
| 25_51006290 | 25 | 51006290 | AG | 0.001512579 | INTRONIC | G |
| 25_51028472 | 25 | 51028472 | GC | 0.001537946 | INTRONIC | G |
| 25_51030165 | 25 | 51030165 | AG | 0.002222301 | INTRONIC | G |
| 25_51063452 | 25 | 51063452 | AG | 0.002408031 | INTRONIC | G |
| 25_51034440 | 25 | 51034440 | CT | 0.004776734 | INTRONIC | C |
| 25_51023068 | 25 | 51023068 | CT | 0.004995797 | SYNONYMOUS_CODING | T |
| 25_51038074 | 25 | 51038074 | CT | 0.005289604 | SYNONYMOUS_CODING | C |
| 25_51029326 | 25 | 51029326 | AG | 0.006052002 | SPLICE_SITE, INTRONIC | A |
| 25_51042357 | 25 | 51042357 | CT | 0.006096905 | INTRONIC | T |
| 25_51040505 | 25 | 51040505 | AG | 0.008742879 | SYNONYMOUS_CODING | A |

3.1.4 CDP-diacylglycerol Synthase (Phosphatidate Cytidylyltransferase) 1 (CDS1)

CDS1 is associated with phospholipid processes (specifically phosphatidic acid). Phospholipids are known to be present in the epiphysis during bone development and important for the process of ossification.

| SNP | chr | loc | bases | chisquared p-value | Consequence | Risk allele |
|---|---|---|---|---|---|---|
| 32_11331413 | 32 | 11331413 | AC | 0.001075223 | UPSTREAM | A |
| 32_11360412 | 32 | 11360412 | TG | 0.001075223 | INTRONIC | T |
| 32_11362156 | 32 | 11362156 | AG | 0.001075223 | INTRONIC | G |
| 32_11366128 | 32 | 11366128 | CT | 0.001075223 | SYNONYMOUS_CODING | C |
| 32_11376468 | 32 | 11376468 | TG | 0.001075223 | DOWNSTREAM | T |
| 32_11376837 | 32 | 11376837 | TG | 0.001075223 | DOWNSTREAM | G |
| 32_12479099 | 32 | 12479099 | AG | 0.00310853 | INTRONIC | A |
| 32_11365955 | 32 | 11365955 | AG | 0.003405422 | INTRONIC | G |
| 32_11366052 | 32 | 11366052 | CT | 0.003405422 | INTRONIC | T |
| 32_11371139 | 32 | 11371139 | TG | 0.00357688 | INTRONIC | G |
| 32_11365924 | 32 | 11365924 | CT | 0.004943424 | INTRONIC | T |
| 32_11360206 | 32 | 11360206 | TG | 0.006457899 | INTRONIC | T |
| 32_11378017 | 32 | 11378017 | AG | 0.009708353 | DOWNSTREAM | A |

3.1.5 Inositol Polyphosphate-5-phosphatase (INPP5D)

INPP5D has been associated with longer lived osteoclasts and altered bone makeup.

| SNP | chr | loc | bases | chisquared p-value | Consequence | Risk allele |
|---|---|---|---|---|---|---|
| 25_47684060 | 25 | 47684060 | TC | 0.000562515 | INTRONIC | C |
| 25_47664131 | 25 | 47664131 | CT | 0.001731421 | SYNONYMOUS_CODING | C |
| 25_47684091 | 25 | 47684091 | TC | 0.002982322 | INTRONIC | C |
| 25_47685188 | 25 | 47685188 | CT | 0.003885197 | INTRONIC | T |
| 25_47666842 | 25 | 47666842 | AG | 0.006492169 | SYNONYMOUS_CODING | G |

3.1.6 SH3-domain Binding Protein 4

Unlike many of the other identified mutations in genes, SH3BP4 does not have a direct connection to bone growth. SH3BP4 is however "involved in cargo-specific control of clathrin-mediated endocytosis, specifically controlling the internalization of a specific protein receptor" (NCBI, 2011).

| SNP | chr | loc | bases | chisquared p-value | Consequence | Risk allele |
|---|---|---|---|---|---|---|
| 25_49142073 | 25 | 49142073 | CT | 0.001744908 | UPSTREAM | T |

3.1.7 Histone Deacetylase 4

In mouse models, HDAC4 impacts chondrocyte hypertrophy by inhibiting the activity of Runx2. HDAC4-null mice displayed premature ossification of developing bones due to ectopic and early chondrocyte hypertrophy.

If the HDAC4 mutation is functional nose morphology changes may occur, as mutations in Runx2 have been associated with nose bridge length across mammalian species.

| SNP | chr | loc | bases | chisquared p-value | Consequence | Risk allele |
|---|---|---|---|---|---|---|
| 25_52402027 | 25 | 52402027 | CT | 0.003226052 | INTRONIC | T |

3.1.8 Leucine Rich Repeat Protein 1

LRR1, also known as PPIL5 is known to regulate the 4-1BB-mediated signalling cascade that results in activation of NFKB and JNK1.

| SNP | chr | loc | bases | chisquared p-value | Consequence | Risk allele |
|---|---|---|---|---|---|---|
| 8_29247021 | 8 | 29247021 | TC | 0.00482 | DOWNSTREAM | T |

3.1.9 v-ski Sarcoma Viral Oncogene Homolog

Mutations in this gene have been associated with many bone morphology and growth speed phenotypes.

| SNP | chr | loc | bases | chisquared p-value | Consequence | Risk allele |
|---|---|---|---|---|---|---|
| 5_60210935 | 5 | 60210935 | AC | 0.005240815 | NON_SYNONYMOUS_CODING | C |

3.1.10 PTGDR

| SNP | chr | loc | bases | chisquared p-value | Consequence | Risk allele |
|---|---|---|---|---|---|---|
| 8_31494277 | 8 | 31494277 | CT | 0.00473 | DOWNSTREAM | C |
| 8_31494760 | 8 | 31494760 | CA | 0.00615 | DOWNSTREAM | C |

4. A Potential Etiology

4.1 CHD, a Disease of Mild Congenital Muscle Pathology?

The mutations discovered in the sequencing project are mainly within genes linked to growth rate and a form of muscular dystrophy, 'Congenital Merosin Deficient Muscular Dystrophy' or CMD (see Table 3).

TABLE 3

Summary of the genes found to have functional mutations.

| Gene | Location | Mutations | Most significant p-value | Connection to CHD |
|---|---|---|---|---|
| Laminin alpha 2 subunit Fragment | Chromosome 1: 70,790,697-71,150,490 | one synonymous coding mutation, one non-synonymous mutation, but less significant. | 1.17E−04 | Muscular dystrophy |
| LSM4 homolog, U6 small nuclear RNA associated | Chromosome 20: 47,714,464-47,721,805 | no coding mutations | 2.18E−04 | Growth rate |
| Collagen, type VI, alpha 3 | Chromosome 25: 50,995,186-51,063,665 | six synonymous coding mutations, one splice site mutation | 9.40E−04 | Muscular dystrophy |
| CDP-diacylglycerol synthase (phosphatidate cytidylyltransferase) 1 | Chromosome 32: 11,331,461-11,375,767 | one synonymous coding mutation | 1.08E−03 | Growth rate |
| inositol polyphosphate-5-phosphatase | Chromosome 25: 47,629,437-47,731,096 | two synonymous coding mutations | 1.73E−03 | Growth rate |
| SH3-domain binding protein 4 | Chromosome 25: 49,142,306-49,155,351 | one upstream mutation | 1.74E−03 | Unknown |
| histone deacetylase 4 | Chromosome 25: 52,342,017-52,443,682 | one intronic mutation | 3.23E−03 | Muscular dystrophy/ Growth rate |
| Leucine rich repeat protein 1 | Chromosome 8: 29,236,409-29,246,995 | one downstream, potentially in UTR | 4.82E−03 | Muscular dystrophy |
| v-ski sarcoma viral oncogene homolog | Chromosome 5: 60,146,103-60,213,750 | one non-synonymous coding mutation | 5.24E−03 | Growth rate | also PTGDR as described above.

The invention claimed is:
1. A method of breeding or preventively treating a first dog having genetic inheritance of Labrador Retriever breed, comprising
(a) genotyping a biological sample obtained from the first dog to determine the presence of T allele or A allele at 1_70997779 in the Laminin alpha 2 subunit Fragment in the genome of the first dog; and
(b) breeding the first dog if A allele is present at 1_70997779 in the Laminin alpha 2 subunit Fragment, or
administering a preventive measure for hip dysplasia to the first dog if T allele is present at 1_70997779 in the Laminin alpha 2 subunit Fragment.
2. The method of claim 1, further comprising collecting a biological sample from a second dog of the opposite sex of the first dog.
3. The method of claim 2, further comprising genotyping the biological sample from the second dog to determine the presence or absence of T allele at 1_70997779 in the Laminin alpha 2 subunit Fragment in the biological sample from the second dog.
4. The method of claim 3, wherein the first dog and the second dog are only bred if T allele is absent at 1_70997779 in the Laminin alpha 2 subunit Fragment in the biological sample from one of the dogs.
5. The method of claim 3, wherein the first dog and the second dog are only bred if T allele is absent at 1_70997779 in the Laminin alpha 2 subunit Fragment in biological samples from both dogs.

* * * * *